(12) United States Patent
Dubbe et al.

(10) Patent No.: US 6,554,614 B1
(45) Date of Patent: Apr. 29, 2003

(54) DENTAL HANDPIECE BRUSH AND METHOD OF USING THE SAME

(75) Inventors: John W. Dubbe, Oakdale, MN (US); Yvonne I. Lund, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/848,028

(22) Filed: May 3, 2001

(51) Int. Cl.[7] .............................. A61C 3/06; A46B 9/04
(52) U.S. Cl. ...................... 433/125; 433/166; 15/167.1; 15/207.2
(58) Field of Search ................................ 433/216, 125, 433/166, 165; 15/167.1, 207.2, DIG. 6

(56) References Cited

U.S. PATENT DOCUMENTS

| | | | |
|---|---|---|---|
| 2,911,660 A | * 11/1959 | Klemas et al. | |
| 2,927,336 A | 3/1960 | Sauer | |
| 3,195,537 A | 7/1965 | Blasi | |
| 3,463,994 A | * 8/1969 | Spohr | |
| 3,618,154 A | * 11/1971 | Muhler et al. | |
| 3,740,853 A | 6/1973 | Brahler | |
| 3,858,368 A | 1/1975 | Cocherell et al. | |
| 3,921,298 A | 11/1975 | Fattaleh | |
| 4,055,897 A | 11/1977 | Brix | |
| 4,561,214 A | 12/1985 | Inoue | |
| 4,739,532 A | 4/1988 | Behrend | |
| 4,827,552 A | * 5/1989 | Bojar et al. | |
| 4,869,277 A | 9/1989 | Olsen | |
| 5,071,348 A | 12/1991 | Woog | |
| 5,099,536 A | 3/1992 | Hirabayashi | |
| 5,211,560 A | 5/1993 | Lowder et al. | |
| 5,273,558 A | 12/1993 | Nelson et al. | |
| 5,273,559 A | 12/1993 | Hammar et al. | |
| 5,276,935 A | * 1/1994 | Lemon et al. | |
| 5,460,883 A | 10/1995 | Barber, Jr. et al. | |
| 5,584,690 A | 12/1996 | Maassarani | |
| 5,660,546 A | 8/1997 | Shafer | |
| 5,679,067 A | 10/1997 | Johnson et al. | |
| 5,827,064 A | * 10/1998 | Bock | 433/216 |
| 5,849,052 A | 12/1998 | Barber, Jr. | |
| 5,903,951 A | 5/1999 | Ionta et al. | |
| 5,915,436 A | 6/1999 | Johnson et al. | |
| 5,983,434 A | 11/1999 | Eichinger et al. | |
| 6,019,603 A | 2/2000 | Von Weissenfluh | |
| 6,126,533 A | 10/2000 | Johnson et al. | |
| 6,163,918 A | * 12/2000 | Weihrauch | 15/207.2 |
| 6,312,257 B1 | * 11/2001 | Aschmann et al. | 433/165 |
| 2001/0007161 A1 | 7/2001 | Masterman et al. | |

* cited by examiner

*Primary Examiner*—Ralph A. Lewis
(74) *Attorney, Agent, or Firm*—James D. Christoff

(57) ABSTRACT

A dental brush has a plurality of bristles and is adapted to connect to a dental handpiece. As the brush is rotated, outer portions of the bristles shift and present an overall tapered configuration with a narrowed outer tip when the bristles come into contact with dental structure. The tapered configuration is particularly useful for finishing and polishing recesses in the patient's tooth structure such as interproximal areas, grooves located next to cusps of the teeth and recesses that may be present in dental restorations.

23 Claims, 3 Drawing Sheets

DENTAL HANDPIECE BRUSH AND METHOD OF USING THE SAME

BACKGROUND OF THE INVENTION

1. Field of the Invention

This invention relates to a rotatable brush for use with dental handpieces. The brush is useful for finishing and polishing a variety of dental structures such as tooth surfaces, direct restorations and indirect restorations.

2. Description of the Related Art

A variety of dental devices for finishing and polishing dental structures are known in the art. Many of these devices are adapted to be connected to a dental handpiece having a rotary drive. If the device is used within the oral cavity of a patient, a releasable connection between the handpiece and the device enables the practitioner to detach the device for disposal or for disinfection before use with a subsequent patient.

Certain types of dental finishing and polishing devices are made of a mixture of a base material such as synthetic resin and an abrasive material such as particles of alumina or zirconia. The synthetic resin is often made of a flexible material that enables the device to bend and deform during use in order to facilitate contact with irregular dental structures as the device is rotating. A wide variety of shapes of such devices are available, including disk shapes, cup shapes, flame shapes and cones or "points".

For example, cup-shaped dental polishers are often considered as best suited for polishing occlusal surfaces of teeth, because the cusps of the teeth can be received within the recess of the cup. On the other hand, dental polishers having a cone-shaped configuration or flame-shaped configuration are often considered best suited for polishing fissures and interproximal surfaces of teeth, since the tip of the cone is better adapted to reach within narrow recesses. Disk-shaped polishers are often thought to best treat the front or labial surfaces of teeth, because the disk is better adapted to contact a larger area of a relatively flat surface when the device is rotating.

Other types of finishing and polishing devices used with dental hand pieces are made of a plurality of bristles that are connected to a central hub. In some instances, the bristles together present a generally cup-shaped configuration with a central recess and with free ends of the bristles being generally aligned in a common plane. In other instances, the bristles have different lengths and are arranged so that the bristles together present an overall pointed or flame-shaped configuration, with the longer bristles being located near the central, rotational axis of the hub. The bristles are made separately and connected together by clasping the bristles within a recess of a metal hub.

Finishing and polishing dental structures are considered to be important tasks for the practitioner, because smooth surfaces in the oral cavity are less likely to retain plaque over a period of time. Moreover, once the plaque has accumulated, it is somewhat easier to remove plaque from a smooth surface in the oral cavity in comparison to a surface that is rough. Consequently, the practitioner will normally take steps to help ensure that any newly-placed restoration is smooth and free of bumps, pits and the like.

In addition, a restoration with a smooth exterior surface is more comfortable when brought into contact with the tongue, lips or other tissue in the oral cavity. Furthermore, a restoration having a smooth surface is often considered more aesthetically pleasing, because the smooth surface reflects light to a greater extent than a surface that is not as smooth. A smooth surface of a dental restoration reflects light in a manner similar to the reflection of light from adjacent natural tooth enamel, and consequently is less noticeable and tends to blend in with the surfaces of adjacent teeth.

While the dental devices described above are in widespread use today, there is a continuing need to improve the state of the art so that finishing and polishing of dental structures are facilitated and results of the procedure are enhanced. Preferably, any such improvements would also increase the practitioner's efficiency and would not unduly add to the overall cost of the dental treatment.

SUMMARY OF THE INVENTION

The present invention is directed toward an improved dental handpiece brush that is made with a plurality of bristles. When the brush is not in use, the bristles are oriented in a generally parallel array. However, during rotation of the brush, the outer ends of the bristles converge and form an overall tapered configuration with a narrowed outer tip when the bristles come into contact with dental structure. The tapered configuration of the bristles is particularly useful for finishing and polishing recesses in dental structure, such as the interproximal areas between adjacent teeth.

Preferably, the bristles are integrally molded to a hub as a unitary body. The stiffness of each bristle is selected so that each bristle is relatively flexible. Preferably, the stiffness of the bristles enables the bristles to converge at relatively slow rotational speeds and flare outwardly at relatively high rotational speeds and/or when increased pressure is applied so that relatively flat tooth structure, when encountered, can be quickly finished or polished.

The dental brush of the present invention conforms well to a variety of anatomical surfaces of the teeth, including cusps and grooves of occlusal surfaces, recesses defined by interproximal surfaces and labial surfaces that are relatively flat. As such, the practitioner need not use more than one type of brush during a dental finishing and polishing procedure. The independent bristles of the brush also easily bend during contact with gingival tissue so that the likelihood of undue tissue abrasion or damage is avoided.

In more detail, the present invention in one aspect is directed toward a brush for a dental handpiece. The brush includes a hub and a plurality of bristles connected to the hub. Each of the bristles has a longitudinal axis that normally extends along a path parallel to a reference axis. Each of the bristles has a free outer end. The outer ends converge toward each other and together present an overall tapered configuration when the hub is rotated in an arc at a certain speed about the reference axis and the bristles are in contact with dental structure. At least some of the bristles comprise an elastomeric material and a number of abrasive particles distributed throughout the elastomeric material.

The invention is also directed in another aspect toward an integrally molded brush that comprises a hub and a plurality of bristles connected to the hub. Each of the bristles has a longitudinal axis that normally extends along a path parallel to a reference axis, wherein the bristles are integrally molded with the hub, and wherein at least some of the bristles have a stiffness in the range of about 0.015 lb/in. to about 0.4 lb/in.

Another aspect of the present invention is directed toward a method of treating dental structure. The method includes the act of providing a plurality of bristles that are normally oriented when quiescent along respective paths generally parallel to a certain reference axis. The method additionally includes the act of applying the free end of the bristles to the dental structure. The method also includes the act of rotating the bristles in an arc about the reference axis at a speed sufficient to converge a free end of the bristles toward each other to present an overall tapered configuration while the bristles are rotating and in contact with the dental structure.

These and other aspects of the invention are described in more detail in the text that follows and are illustrated in the accompanying drawings.

DETAILED DESCRIPTION OF THE PREFERRED EMBODIMENTS

Figure 1:
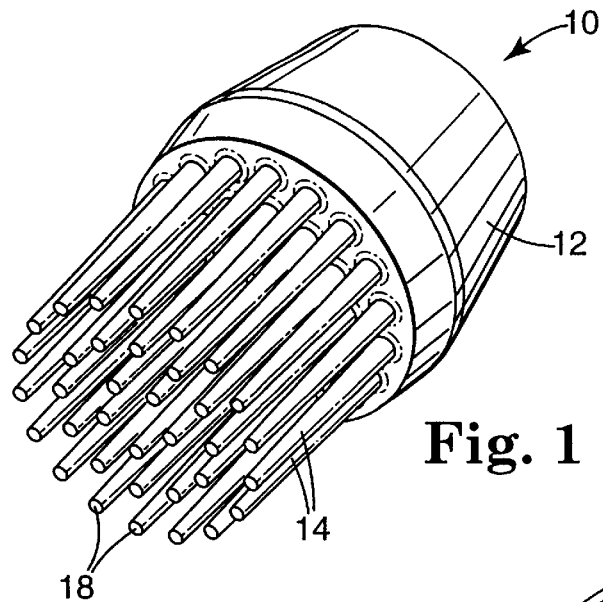
FIG. 1 is a perspective view of a brush for a dental handpiece according to one embodiment of the present invention.

A brush for a dental hand piece that is constructed in accordance with one embodiment of the present invention is illustrated in FIGS. 1–4 and is broadly designated by the numeral 10. The brush 10 includes a central hub 12 along with a plurality of bristles 14 that are connected to the hub 12. In the embodiment shown in the drawings, thirty-five bristles 14 are provided, although as an alternative a larger or smaller number of bristles may also be used.

Figure 2:
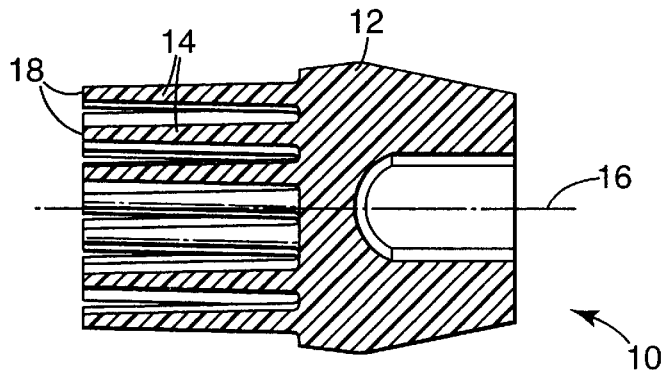
FIG. 2 is an enlarged side cross-sectional view of the brush illustrated in FIG. 1.

Each of the bristles 14 has a longitudinal axis that normally extends along a path generally parallel to a reference axis 16 that is shown in FIG. 2. The reference axis 16 is preferably oriented along a central axis of the hub 12. In use, the brush 10 is rotated in an arc about the central axis 16 as will be described in more detail in the paragraphs that follow.

Figure 3:
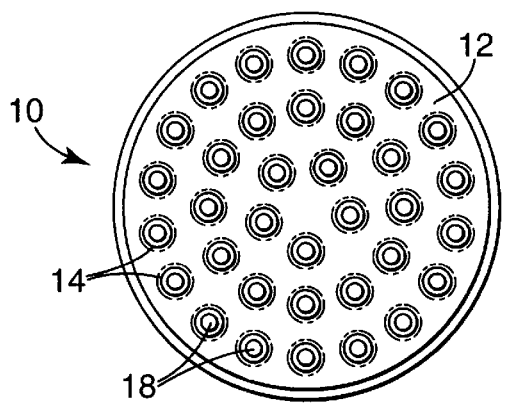
FIG. 3 is an end view of the brush depicted in FIGS. 1 and 2, looking toward a front end of the brush.

Preferably, each of the bristles 14 has a tapered configuration with a cross-sectional shape that decreases in area as a free, outer end 18 of the bristle 14 is approached. An example of a suitable overall taper is 2.4 degrees, although tapers of other magnitude are also possible. Preferably, but not necessarily, the outer ends 18 of all of the bristles 14 lie in a common reference plane that is perpendicular to the central reference axis 16 as shown in FIG. 3.

A number of different constructions of the brush 10 are possible. For example, the overall length of the bristles 14 is preferably in the range of about 0.05 in. (1.3 mm) to about 0.25 in. (6.3 mm), more preferably in the range of about 0.10 in. (2.5 mm) to about 0.2 in. (5 mm) and most preferably in the range of about 0.15 in. (3.8 mm) to about 0.2 in. (5 mm). Additionally, the outer free end 18 of each bristle 14 preferably has a diameter in the range of about 0.008 in. (0.2 mm) to about 0.02 in. (0.5 mm), more preferably in the range of about 0.008 in. (0.2 mm) to about 0.016 in. (0.4 mm) and most preferably in the range of about 0.008 in. (0.2 mm) to about 0.012 in. (0.3 mm). The opposite end of each bristle 14 (i.e., the base of the bristle 14) has a diameter that is preferably in the range of about 0.012 in. (0.3 mm) to about 0.03 in. (0.8 mm), more preferably in the range of about 0.012 in. (0.3 mm) to about 0.02 in. (0.5 mm) and most preferably in the range of about 0.012 in. (0.3 mm) to about 0.016 in. (0.4 mm).

The number of bristles 14 may also vary. The number of bristles 14 is preferably in the range of about 20 to about 60, more preferably in the range of about 30 to about 55 and most preferably in the range of about 35 to about 54. However, a larger or smaller number of bristles 14 is also possible.

The length of the hub 12 in directions along the reference axis 16 may also vary. For example, the overall length of the hub 12 is preferably in the range of about 0.15 in. (3.8 mm) to about 0.25 in. (6.3 mm), more preferably in the range of about 0.175 in. (4.4 mm) to about 0.22 in. (5.6 mm) and most preferably in the range of about 0.175 in. (4.4 mm) to about 0.2 in. (5.1 mm).

The brush 10 including the hub 12 and the bristles 14 is preferably integrally molded as a single unitary component from an elastomeric synthetic resinous material. Examples of suitable elastomeric materials include segmented polyester thermoplastic elastomers, segmented polyamide thermoplastic elastomers, blends of thermoplastic elastomers and thermoplastic polymers, and ionomeric thermoplastic elastomers. Specific examples of a suitable thermoplastic elastomers are "Hytrel" brand elastomer numbers 6356 and 5526, from du Pont.

Preferably, a number of abrasive particles are embedded in the elastomeric material including the bristles 14. Examples of suitable abrasive particles include particles made of fused aluminum oxide, ceramic aluminum oxide, heat-treated aluminum oxide, silicone carbide, titanium diboride, alumina zirconia, diamond, boron carbide, ceria, aluminum silicates, cubic boron nitride, garnet, silica and combinations of those particles. An example of particularly preferred abrasive particles comprises a mixture of aluminum oxide particles and alumina zirconia particles.

Preferably, the abrasive particles have an average size in the range of about 0.1 micrometers to about 1500 micrometers, more preferably in the range of about 1 micrometer to about 1000 micrometers and most preferably in the range of about 50 micrometers to about 500 micrometers. The loading of the particles is preferably in the range of about 10 percent to about 50 percent and more preferably in the range of about 35 percent to about 40 percent by weight. The average particle size is typically measured by the longest dimension.

The abrasive particles can have any precise shape or can be irregularly or randomly shaped. Examples of such three dimensional shapes includes: pyramids, cylinders, cones, spheres, blocks, cubes, polygons, and the like. Alternatively, the abrasive particles can be relatively flat and have a cross sectional shape such as a diamond, cross, circle, triangle, rectangle, square, oval, octagon, pentagon, hexagon, polygon and the like.

Optionally, the resinous material includes a lubricant to reduce the friction of the bristles 14 against the dental structure and the amount of heat that might otherwise be created. Suitable lubricants for some refining applications, it is preferred that the molded polymer 28 include a lubricant.

The presence of a lubricant in the moldable polymer 28 reduces the friction of the bristle contacting the workpiece surface. This reduces the heat generated when refining the workpiece. Excessive heat may cause the brush to leave residue on the workpiece or to otherwise harm the workpiece. Suitable lubricants include lithium stearate, zinc stearate, calcium stearate, aluminum stearate, ethylene bis stearamide, graphite, molybdenum disulfide, polytetraflouroethylene (PTFE), and silicone compounds, for example useful with thermoplastics and thermoplastic elastomers.

An example of a preferred silicone material, which is described in U.S. Pat. No. 5,849,052, incorporated herein by reference, is a high molecular weight polysiloxane of formula (A):

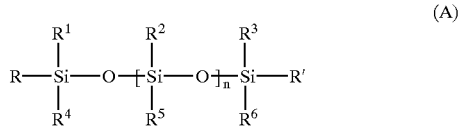

(A)

wherein R, R', $R^1, R^2, R^3, R^4, R^5$, and $R^6$ may be the same or different and can be an alkyl, vinyl, chloroalkyl, aminoalkyl, epoxy, fluororalkyl, chloro, fluoro, or hydroxy, and n is 500 or greater, preferably 1,000 or greater, more preferably 1,000 to 20,000, and most preferably 1,000 to 15,000.

Another preferred polysiloxane is a polydimethylsiloxane of formula (B):

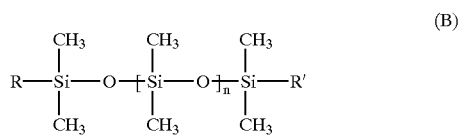

(B)

wherein R and R' may be the same or different and can be an alkyl, vinyl, chloroalkyl, aminoalkyl, epoxy, fluororalkyl, chloro, fluoro, or hydroxy, and n is 500 or greater, preferably 1,000 or greater, more preferably 1,000 to 20,000, and most preferably 1,000 to 15,000.

Polysiloxanes are available in many different forms, e.g., as the compound itself or as a concentrate. Example of the polymers into which the polysiloxane can be compounded include polypropylene, polyethylene, polystyrene, polyamides, polyacetal, acrylonitrile-butadiene-styrene (ABS), and polyester elastomer, all of which are commercially available. Silicone modified Hytrel™ is available commercially as BY27-010 (or MB50-010), and silicone modified Nylon 6.6 is available as BY27-005 (or MB50-005), both from Dow Corning Company, Midland, Mich. Typically, commercially available concentrates may contain a polysiloxane at a weight percent ranging from 40 to 50; however, any weight percent is acceptable for purposes of the invention as long as the desired weight percent in the final product can be achieved. Lubricants preferably can be present in the moldable polymer in amounts of up to about 20 percent by weight (exclusive of abrasive particle content), and preferably in an amount from about 1 to 15 percent, although more or less may be used as desired.

Preferably, each of the bristles 14 has a stiffness in the range of about 0.015 lb/in to about 0.4 lb/in, more preferably in the range of about 0.02 lb/in to about 0.37 lb/in, and most preferably in the range of about 0.02 lb/in to about 0.15 lb/in. The stiffness is determined by measuring the force necessary to displace the outer end 18 of the bristle 14 a certain distance when the opposite end of the same bristle 14 is held in a stationary position. The resulting bristles 14 have been observed to reduce chatter and skip as the brush 10 is moved across a variety of surface configurations. It is believed that during use of the brush 10 having bristles 14 with a stiffness in the ranges set out above, facilitates the finishing and polishing of dental structures because bristles 14 near the middle of the hub 12 can easily deflect to allow remaining bristles 14 near the periphery of the hub 12 to come into a position of better contact with the dental structure. It is believed that such construction provides a better, more uniform distribution of forces against the dental structure of interest, even when the structure is relatively non-planar. Furthermore, in that instance more of the bristles 14 are in contact with the surface.

Preferably, the bristles are made of a material having a flexural modulus that is in the range of about 50,000 psi to about 120,000 psi and more preferably in the range of about 60,000 psi to about 110,000 psi. Most preferably the bristles are made of a material having a flexural modulus in the range of about 65,000 psi to about 100,000 psi. The flexural modulus is determined by following the procedure set out in ASTM D790 and is carried out using the material as molded (i.e., with any abrasive particles, or other additive).

Preferably, each of the bristles 14 has a stiffness in the range of about 0.015 lb/in to about 0.4 lb/in and also has a flexural modulus in the range of about 50,000 psi to about 120,000 psi. More preferably, each of the bristles 14 has a stiffness in the range of about 0.02 lb/in to about 0.37 lb/in and also has a flexural modulus in the range of about 60,000 psi to about 110,000 psi. Most preferably, each of the bristles 14 has a stiffness in the range of about 0.02 lb/in to about 0.15 lb/in and also has a flexural modulus in the range of about 65,000 psi to about 100,000 psi.

An example of a presently preferred brush 10 includes thirty-five bristles 14, each with an overall length of about 0.2 in. (5.1 mm). Each of such bristles 14 has an outer, free end 18 with a diameter of about 0.012 in. (0.3 mm) and a base diameter of about 0.02 in. (0.5 mm). In addition, the overall length of the hub 12 is about 0.2 in. (5.1 mm). The diameter of the hub 12 adjacent the base of the bristles 14 is about 0.25 in. (6.3 mm). Preferably, a small fillet radius (such as 0.005 in. (0.13 mm)) is provided at the base of each bristle 14 for connection to the hub 12, in order to help distribute stresses incurred on the brush 10 during use and also help reduce the likelihood of unintentional detachment of the bristles 14 from the hub 12. This brush 10 is made using a mixture of "Hytrel" brand elastomer, no. 6356 silicon modified "Hytrel" brand lubricant (No. MB50-010) in a quantity of 10% to 12% by weight, and abrasive particles in a quantity of 35%–40% by weight, and the particles are aluminum oxide particles having a size of either 400 grit or 220 grit (as determined by FEPA standards).

A number of other synthetic resinous materials, abrasive particles, lubricants and additives are also possible. Examples of such other materials are set out in applicant's U.S. Pat. Nos. 5,679,067, 5,903,951, 5,915,436, and 6,126, 533, all of which are expressly incorporated by reference herein.

Figure 4:
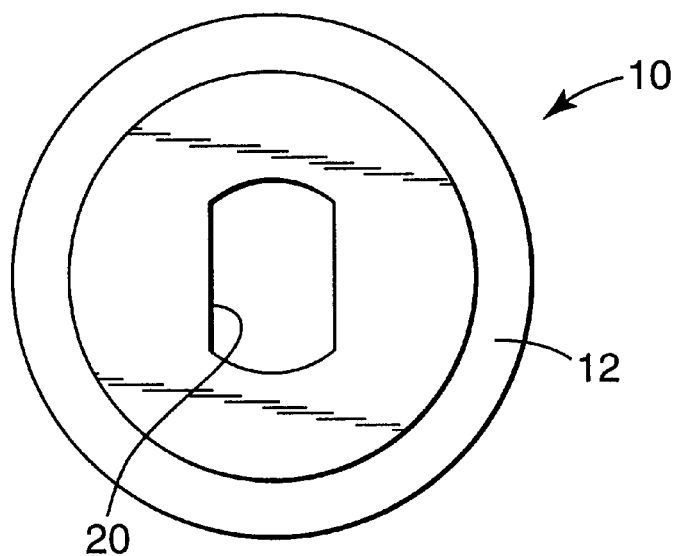
FIG. 4 is an end elevational view of the brush shown in FIGS. 1–3, looking toward a rear end of the brush.

As illustrated in FIG. 4, the hub 12 of the brush 10 includes a recess 20 that extends from the rear end of the hub 12 in a direction toward the bristles 14. The recess 20 has a pair of flat, parallel sides that face each other, along with two curved end walls that interconnect the parallel sides. The recess 20 is adapted to detachably receive a mandrel that, in turn, is connected to a chuck of a dental hand piece.

Figure 5:
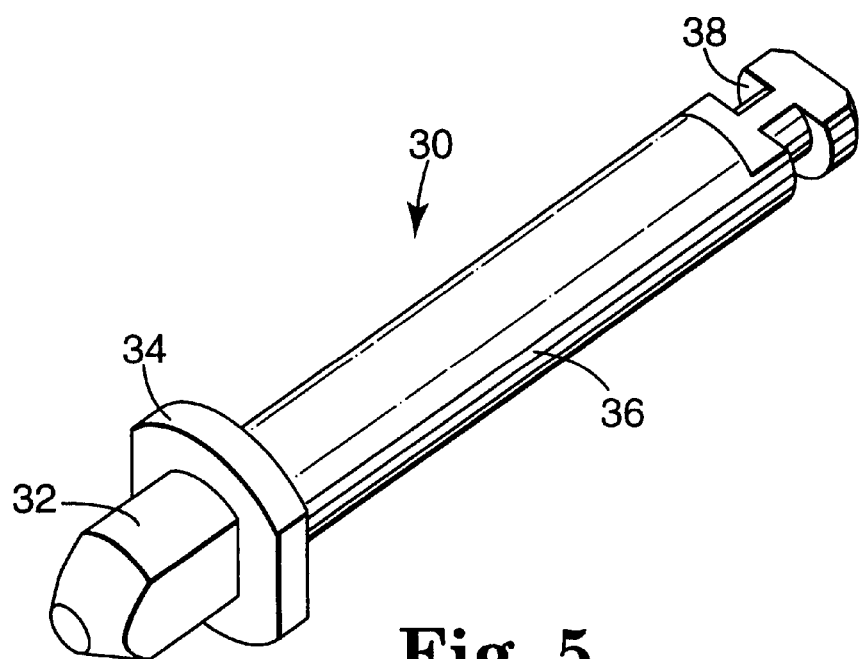
FIG. 5 is a perspective view of a mandrel especially adapted for use with the dental brush shown in FIGS. 1–4.

FIG. 5 illustrates an exemplary mandrel 30 for use with the brush 10. The mandrel 30 includes a tab 32 having a shape that is complementary to the shape of the recess 20. Preferably, the overall shape of the tab 32 in reference planes perpendicular to a central axis of the mandrel 30 is slightly larger than the shape of the recess 20, so that the tab 32 is received in friction-fit relation in the recess 20. The friction-fit relation is sufficiently snug to retain the brush 10 on the mandrel 30 during ordinary use, and yet is constructed so that the brush 10 may be uncoupled from the mandrel 30 by pulling the brush 10 away from the mandrel 30 using finger pressure without undue force.

The mandrel 30 also includes a flange 34 that is located adjacent the tab 32. The flange 34 limits insertion of the tab 32 into the recess 20. In addition, the flange 34 provides a non-yielding surface for contact with the hub 12 during use of the brush 10 to further ensure that the brush 10 does not unduly deform and unintentionally detach from the mandrel 30 during a dental procedure.

The mandrel 30 also includes a shaft 36 having a somewhat cylindrical configuration. An outer end of the shaft 36 includes a flattened region as well as a notch 38 for detachable connection to a quick-release coupling of a dental handpiece drive. A variety of dental handpieces are available, and if desired the configuration of the shaft 36 may be changed from that shown in the drawings in order to matingly fit with a particular handpiece of interest. For example, the shaft may be smooth and lack a notch.

As an alternative, the brush 10 and the mandrel 30 may be permanently connected together. Optionally, the brush 10 and the mandrel 30 are molded simultaneously as a single, unitary component. As another option, the brush 10 and the mandrel 30 are molded by a co-injection process (using similar or dissimilar materials) or molded by an overmolding (or stage molding) process. In any instance, the shaft should be made of a material that is suitable for direct connection to the handpiece and does not break or unduly bend during use.

Figure 6:
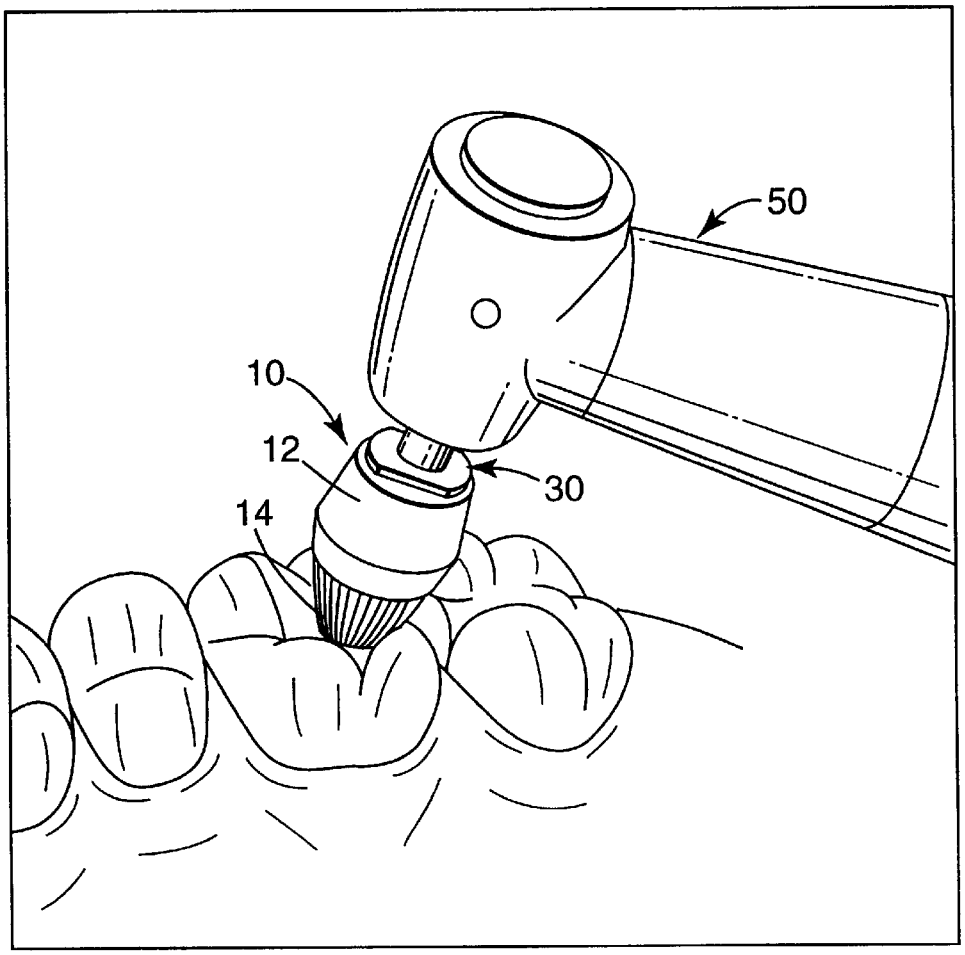
FIG. 6 is a reduced perspective view of one example of use of the dental brush according to the present invention, wherein bristles of the brush tend to converge during rotation of the brush in order to facilitate finishing and polishing of a recess between adjacent teeth of a dental patient.

FIG. 6 is an illustration of an exemplary use of the brush 10 and the mandrel 30 during a dental finishing and polishing procedure. As shown, the brush 10 is connected to the mandrel 30 and the mandrel, in turn, is connected to a dental handpiece 50. When the handpiece 50 is activated, the brush 10 is rotated about the central reference axis 16. Preferably, the rotation speed is in the range of about 4000 rpm to abaout 12,000 rpm. Slower or higher rotation speeds may also be used.

As the hub 12 is rotated about the reference axis 16, the outer ends 18 of the bristles 14 tend to converge when in contact with dental structure. When converged, the bristles 14 together present an overall tapered, frustoconical configuration, with the outer ends 18 all simultaneously contacting the outer ends 18 of each adjacent bristle 18. As such, essentially more of the outer ends 18 are spaced from the outer ends 18 of adjacent bristles. Preferably, the outer portions of the bristles 14 extending toward a point that is spaced from the outer ends 18. As an alternative, however, the bristles 14 could be shaped so that the outer portion of the bristles 14 together present an overall conical configuration as the hub 12 is rotated.

The example of use shown in FIG. 6 illustrates the bristles 14 converging toward a generally overall frustoconical configuration. The tapered shape represents the overall shape of the combined bristles 14 and not merely the bristles 14 that are currently in contact with the structure as the brush 10 rotates. This tapered shape is particularly useful for finishing and polishing recesses in dental structure. Examples of recesses in dental structure include areas (such as grooves) adjacent cusps of the teeth as shown in FIG. 6.

However, other examples of suitable recesses in dental structure include fissures, interproximal areas and cavity preparations of natural tooth structure. Moreover, the recesses can include a surface of a crown, bridge or other restoration. If desired, the brush 10 may be applied to the recess of an indirect restoration before such time as the restoration is placed in the oral cavity of the patient.

In certain instances, the bristles 14 of the dental brush 10 may tend to flare outwardly instead of converging when the bristles 14 come into contact with a relatively flat surface and the reference axis 16 is perpendicular to that surface. Flaring of the bristles 14 may be observed during rotation of the hub 12 at higher speeds and/or increased pressure against the dental structure. Such flaring-out motion enables the practitioner to quickly finish and polish relatively large areas of tooth structure and restorations such as labial or front surfaces of the patient's teeth. The flared configuration helps to reduce the time needed for the practitioner to complete the treatment, so that both the practitioner and the patient can realize a savings of time.

Another advantage of the dental brush 10 is that the bristles 14 are able to shift independently of each other during use and can easily bend or deform when contact with oral tissue is made. As a result, the bristles can easily bend during use to help conform to the shape of the surface of interest. In addition, the independently movable bristles 14 are less likely to injure gingival tissue or other soft tissue in the patient's oral cavity in instances where the brush 10 inadvertently contacts the same.

The brush 10 is useful in orthodontic procedures as well. For example, the brush 10 may be used to prepare a surface of a tooth prior to bonding an orthodontic bracket to the tooth. Additionally, the brush 10 may be used to remove adhesive from the enamel surface of the teeth once the brackets are detached at the conclusion of orthodontic treatment.

In general, the abrasive particles embedded in the bristles 14 obviate the need to use a paste for polishing the dental structures. However, a paste may be used with the brush 10 if desired. If a paste is used, the tendency of the bristles 14 to converge inwardly may help retain the paste in the brush 10, such that less paste is ejected free of the bristles 14 and wasted.

Those skilled in the art will recognize that a variety of modifications and additions may be made to the brush 10 without departing from the spirit of the invention. Accordingly, the invention should not be deemed limited to the particular constructions and methods of use as set out in detail above and in the accompanying drawings, but instead only by a fair scope of the claims that follow along with their equivalents.

What is claimed is:

1. A brush for a dental handpiece comprising:

a hub having a central reference axis; and a plurality of bristles connected to the hub, each of the bristles having a longitudinal axis that normally extends along a path parallel to the reference axis, each of the bristles having a free outer end, wherein the outer ends converge toward each other and together present an overall tapered configuration when the hub is rotated in an arc at a certain speed about the reference axis and bristles are in contact with dental structure, and wherein at least some of the bristles comprise an elastomeric material and a number of abrasive particles distributed throughout the elastomeric material.

2. A brush for a dental handpiece according to claim 1 wherein the hub is integrally connected to the bristles.

3. A brush for a dental handpiece according to claim 2 wherein the bristles are made of a thermoplastic material.

4. A brush for a dental handpiece according to claim 1 wherein all of the bristles are made of an elastomeric material.

5. A brush for a dental handpiece according to claim 4 wherein the bristles are injection molded.

6. A brush for a dental handpiece according to claim 5 wherein the particles are comprised of aluminum oxide particles, aluminum zirconia particles or a combination of aluminum oxide particles and aluminum zirconia particles.

7. A brush for a dental handpiece according to claim 1 wherein each of the bristles has a generally tapered configuration with a cross-sectional shape that decreases in area as the outer end is approached.

8. A brush for a dental handpiece according to claim 1 wherein the overall tapered configuration of the bristles is a frustoconical configuration.

9. A brush for a dental handpiece according to claim 1 wherein the overall tapered configuration of the bristles is a conical configuration.

10. A brush for a dental handpiece according to claim 1 and including a mandrel detachably connected to the hub.

11. A brush for a dental handpiece according to claim 1 wherein at least some of the bristles have a stiffness in the range of about 0.015 lb/in to about 0.4 lb/in.

12. A brush for a dental handpiece according to claim 11 wherein each bristle is made of a material having a flexural modulus in the range of about 50,000 psi to about 120,000 psi.

13. A brush for a dental handpiece according to claim 1 wherein at least some of the bristles have a stiffness in the range of about 0.02 lb/in to about 0.37 lb/in and is made of a material having a flexural modulus in the range of about 60,000 psi to about 110,000 psi.

14. A brush for a dental handpiece according to claim 1 wherein the outer end of substantially each bristle is in contact with the outer end of each adjacent bristle when the outer ends converge toward each other.

15. A brush for a dental handpiece according to claim 1 wherein the bristles comprise a thermoplastic material having a flexural modulus in the range of about 50,000 psi to about 120,000 psi.

16. A method of treating dental structure comprising:
providing a hub and a plurality of bristles connected to the hub, wherein the hub has a central axis, and wherein the bristles are normally oriented when quiescent along respective paths generally parallel to the reference axis;
applying the free end of the bristles to the dental structure; and
rotating the bristles in an arc about the reference axis at a speed sufficient to converge a free end of the bristles toward each other to present an overall tapered configuration while the bristles are rotating and in contact with the dental structure.

17. A method of treating dental structure according to claim 16 wherein the act of applying the free end of the bristles to the dental structure includes the act of polishing the dental structure.

18. A method of treating dental structure according to claim 16 wherein the act of applying the free end of the bristles to the dental structure includes the act of finishing the dental structure.

19. A method of treating dental structure according to claim 16 wherein the overall tapered configuration is a conical configuration.

20. A method of treating dental structure according to claim 16 wherein the overall tapered configuration is a frustoconical configuration.

21. A method of treating dental structure according to claim 16 wherein each of the bristles has an overall tapered configuration.

22. A method of treating dental structure according to claim 16 wherein the act of providing a plurality of bristles includes the act of providing at least some of the bristles with abrasive particles.

23. A method of treating dental structure according to claim 16 wherein the act of providing a plurality of bristles includes the act of providing a unitary body that includes a hub and the bristles.

* * * * *